US011413403B2

(12) United States Patent
Yoshioka et al.

(10) Patent No.: US 11,413,403 B2
(45) Date of Patent: Aug. 16, 2022

(54) INFUSION SYSTEM

(71) Applicant: MED-TECH INC., Tokyo (JP)

(72) Inventors: Noriaki Yoshioka, Saitama (JP);
Soichiro Okazaki, Saitama (JP); Taro
Taketomi, Hyogo (JP)

(73) Assignee: MED-TECH INC., Tokyo (JP)

( * ) Notice: Subject to any disclaimer, the term of this patent is extended or adjusted under 35 U.S.C. 154(b) by 0 days.

(21) Appl. No.: 16/318,913

(22) PCT Filed: Sep. 7, 2017

(86) PCT No.: PCT/JP2017/032235
§ 371 (c)(1),
(2) Date: Jan. 18, 2019

(87) PCT Pub. No.: WO2018/074089
PCT Pub. Date: Apr. 26, 2018

(65) Prior Publication Data
US 2019/0240424 A1 Aug. 8, 2019

(30) Foreign Application Priority Data
Oct. 21, 2016 (JP) .............................. JP2016-206891

(51) Int. Cl.
A61M 5/44 (2006.01)
A61M 5/36 (2006.01)
(Continued)

(52) U.S. Cl.
CPC ................ A61M 5/44 (2013.01); A61M 5/14
(2013.01); A61M 5/142 (2013.01); A61M 5/36
(2013.01);
(Continued)

(58) Field of Classification Search
CPC .......... A61M 5/44; A61M 5/14; A61M 5/142;
A61M 5/36; A61M 5/365; A61M 1/166;
(Continued)

(56) References Cited
U.S. PATENT DOCUMENTS 4,065,264 A * 12/1977 Lewin ...................... A61M 1/32
422/46
4,160,801 A * 7/1979 Badolato ................. A61M 1/32
128/DIG. 3
(Continued)

FOREIGN PATENT DOCUMENTS

CN 202168979 U 3/2012
CN 104162198 A 11/2014
(Continued)

OTHER PUBLICATIONS

Official Communication issued in International Bureau of WIPO Patent Application No. PCT/JP2017/032235, dated Oct. 3, 2017.
(Continued)

Primary Examiner — Amber R Stiles
Assistant Examiner — Avery Smale
(74) Attorney, Agent, or Firm — Greenblum & Bernstein, P.L.C.

(57) ABSTRACT

Provided is an infusion system including: a liquid container that accommodates a blood derivative; a heating device that heats the blood derivative; an air bubble removal chamber that removes air bubbles in the blood derivative; a first flow path that connects the liquid container and the heating device to each other; a second flow path that connects the heating device and the air bubble removal chamber to each other; a third flow path that connects the air bubble removal chamber and an infusion unit to each other; a fourth flow path that connects the air bubble removal chamber and the liquid container to each other; a first pump provided in the
(Continued)

first flow path; and a second pump provided in the third flow path. The heating device has a heating flow path where the blood derivative flows and a heat supply body that contacts the heating flow path.

16 Claims, 3 Drawing Sheets

(51) Int. Cl.
*A61M 5/142* (2006.01)
*A61M 5/14* (2006.01)

(52) U.S. Cl.
CPC ..... *A61M 5/365* (2013.01); *A61M 2205/3368* (2013.01); *A61M 2205/36* (2013.01)

(58) Field of Classification Search
CPC ...... A61M 2205/36; A61M 2205/3368; A61M 5/1411; A61M 5/168; A61M 5/16877; A61M 5/172; A61M 2205/3379
See application file for complete search history.

(56) References Cited

U.S. PATENT DOCUMENTS

| | | | | |
|---|---|---|---|---|
| 4,874,359 | A | * | 10/1989 | White ................ A61M 1/3621 604/6.09 |
| 5,211,201 | A | * | 5/1993 | Kamen ................ A61M 5/162 137/1 |
| 7,819,835 | B2 | | 10/2010 | Landy et al. |
| 2004/0019320 | A1 | * | 1/2004 | Childers ............... A61M 1/284 604/29 |
| 2006/0211986 | A1 | | 9/2006 | Smisson, III et al. |
| 2011/0040229 | A1 | | 2/2011 | Hannan et al. |
| 2012/0123257 | A1 | | 5/2012 | Stokes, Jr. et al. |
| 2012/0305090 | A1 | | 12/2012 | Bene |
| 2012/0306881 | A1 | | 12/2012 | Nemoto |
| 2015/0305985 | A1 | | 10/2015 | Norman et al. |

FOREIGN PATENT DOCUMENTS

| | | | |
|---|---|---|---|
| JP | 62-253076 | | 11/1987 |
| JP | 2002-102349 | A | 4/2002 |
| JP | 2005-131077 | | 5/2005 |
| JP | 2005-131078 | | 5/2005 |
| JP | 2005131078 | A * | 5/2005 |
| JP | 2008-532695 | | 8/2008 |
| JP | 2011-010694 | | 1/2011 |
| JP | 2011010694 | A * | 1/2011 |
| JP | 2013-500060 | A | 1/2013 |
| JP | 2013-501578 | | 1/2013 |
| JP | 2013-94473 | A | 5/2013 |
| JP | 2013-514839 | A | 5/2013 |
| JP | 2013-106976 | | 6/2013 |
| JP | 2015-073848 | | 4/2015 |
| JP | 2015073848 | A * | 4/2015 |
| WO | 2012/105577 | A1 | 8/2012 |

OTHER PUBLICATIONS

International Preliminary Report on Patentability received in International Application No. PCT/JP2017/032235, dated Apr. 23, 2019.

* cited by examiner

INFUSION SYSTEM

TECHNICAL FIELD

The present application is a 371 National Stage Application of PCT/JP2017/032235, filed Sep. 7, 2021 and is based on Japanese Patent Application No. 2016-206891 filed on Oct. 21, 2016, the entire contents of which are incorporated herein by reference.

The present invention relates to an infusion system.

BACKGROUND ART

In hospitals, blood derivatives are stored under refrigeration to maintain the functions of the blood derivatives that are to be infused into patients. In infusing a blood derivative into a patient, the blood derivative may be heated to an appropriate temperature to lighten a burden on the patient. In particular, in case of massive or critical bleeding, a blood derivative is required to be massively infused in a short time. In this case, the blood derivative is required to be rapidly heated to the temperature of a patient in order to prevent hypothermia.

Conventionally, infusion systems with which a blood derivative is infused into a patient while being heated have been known to treat the patient causing the above massive or critical bleeding. The infusion systems are constituted by tubes or pumps that feed a blood derivative, a heating device that heats the blood derivative to a prescribed temperature, or the like. The heating device requires high-efficiency heating to enable massive infusion in a short time.

As a method for heating a blood derivative highly efficiently, there has been known a method in which a metal member that generates heat with induction heating is brought into direct contact with the blood derivative to perform heat exchange (see Patent Document 1). The direct exchange of heat between the metal member and the blood derivative results in good heating efficiency, but a portion that is to be discarded after use contains the expensive metal member. Therefore, the use of the metal member in this method is costly.

CITATION LIST

Patent Document

Patent Document 1: U.S. Pat. No. 7,819,835 (Specification)

SUMMARY

Technical Problem

On the other hand, instead of the above method in which a metal member is brought into direct contact with a blood derivative, there is considered to be a method in which heat is supplied from an outside to an inexpensive and flexible heating flow path. In this case, heating efficiency reduces compared with the above method. Therefore, thinning of the wall surface of the heating flow path and widening of the flow path area of the heating flow path are considered to be required.

In such a situation, however, the blood derivative is required to be fed to the heating flow path at a high pressure by a pump. Therefore, the internal pressure of the heating flow path increases, and the heating flow path expands. Thus, a structure that firmly presses the heating flow path against the heating device is required, which results in an increase in the weight of the heating device. In addition, when the structure that presses the heating device has large heat capacity, the heating efficiency is also affected. Moreover, when an infusion amount for a patient is changed, for example, from a high flow rate to a low flow rate, there is a likelihood that heat accumulated in the peripheral part of the heating flow path transfers to the blood derivative to cause an excessive increase in the temperature of the blood derivative. The blood derivative is morphologically and functionally abnormalized or hemolyzed when heated to a high temperature. Therefore, there is an upper limit temperature at which the blood derivative can be maintained (in a favorable state) so as not to be abnormalized or hemolyzed. When the blood derivative is heated with its upper limit temperature set at about 42° C., it is important to perform control so that the blood derivative does not exceed the temperature.

Further, since air bubbles are generated when the blood derivative is heated, it is required to catch the generated air bubbles with an air bubble removal chamber to prevent the air bubbles from being injected into a patient in such an infusion system. However, in conventional infusion systems, there is a likelihood that air bubbles flow into the downstream of an air bubble removal chamber and are injected into a patient when the air bubbles are accumulated in the air bubble removal chamber and a liquid level is lowered. Therefore, it is required to perform the operation of stopping infusion periodically and removing the air bubbles.

The present application has been made in view of such points and has an object of providing an infusion system capable of decreasing the internal pressure of a heating flow path, properly performing the temperature control of a liquid for infusion such as a blood derivative in response to the fluctuation of an infusion amount, and performing the removal of air bubbles without stopping the infusion.

Solution to Problem

After an intensive study, the present inventors have found that the above problems can be solved with, for example, the provision of a pump in a flow path that connects an air bubble removal chamber and an infusion unit, which performs infusion, to each other, and thus have come to the completion of the present invention.

That is, the present invention includes the following modes.

(1) An infusion system including: a liquid container that accommodates a liquid for infusion; a heating device that heats the liquid; an air bubble removal chamber that removes air bubbles in the liquid; a first flow path that connects the liquid container and the heating device to each other; a second flow path that connects the heating device and the air bubble removal chamber to each other; a third flow path that connects the air bubble removal chamber and an infusion unit, which performs the infusion, to each other; a fourth flow path that connects the air bubble removal chamber and the liquid container to each other; a first pump provided in the first flow path; and a second pump provided in the third flow path, wherein the heating device has a heating flow path where the liquid flows and a heat supply body that contacts the heating flow path to supply heat to the heating flow path.

(2) The infusion system according to (1), further including an air bubble detector that detects air bubbles passing through the second flow path.

(3) The infusion system according to (2), further including a control device that controls the first pump to increase a liquid feeding flow rate of the first pump when the air bubbles are detected by the air bubble detector.

(4) The infusion system according to any one of (1) to (3), further including a liquid level detector that detects a liquid level inside the air bubble removal chamber.

(5) The infusion system according to (4), further including a control device that controls the first pump to increase a liquid feeding flow rate of the first pump when the liquid level detected by the liquid level detector is lower than a prescribed threshold.

(6) The infusion system according to any one of (1) to (5), wherein the first pump and the second pump have a liquid feeding capacity of 100 ml/min or more.

(7) The infusion system according to any one of (1) to (6), wherein the heating flow path is constituted by a flexible tube.

(8) The infusion system according to (7), wherein the flexible tube has a thickness of 0.4 mm or less.

(9) The infusion system according to any one of (1) to (8), wherein the heating flow path has a flow path area of 200 $cm^2$ or more.

Advantageous Effects of Invention

According to the present invention, an infusion system capable of decreasing the internal pressure of a heating flow path, properly performing the temperature control of a liquid for infusion in response to the fluctuation of an infusion amount, and performing the removal of air bubbles without stopping the infusion can be provided.

DESCRIPTION OF EMBODIMENTS

Figure 1:
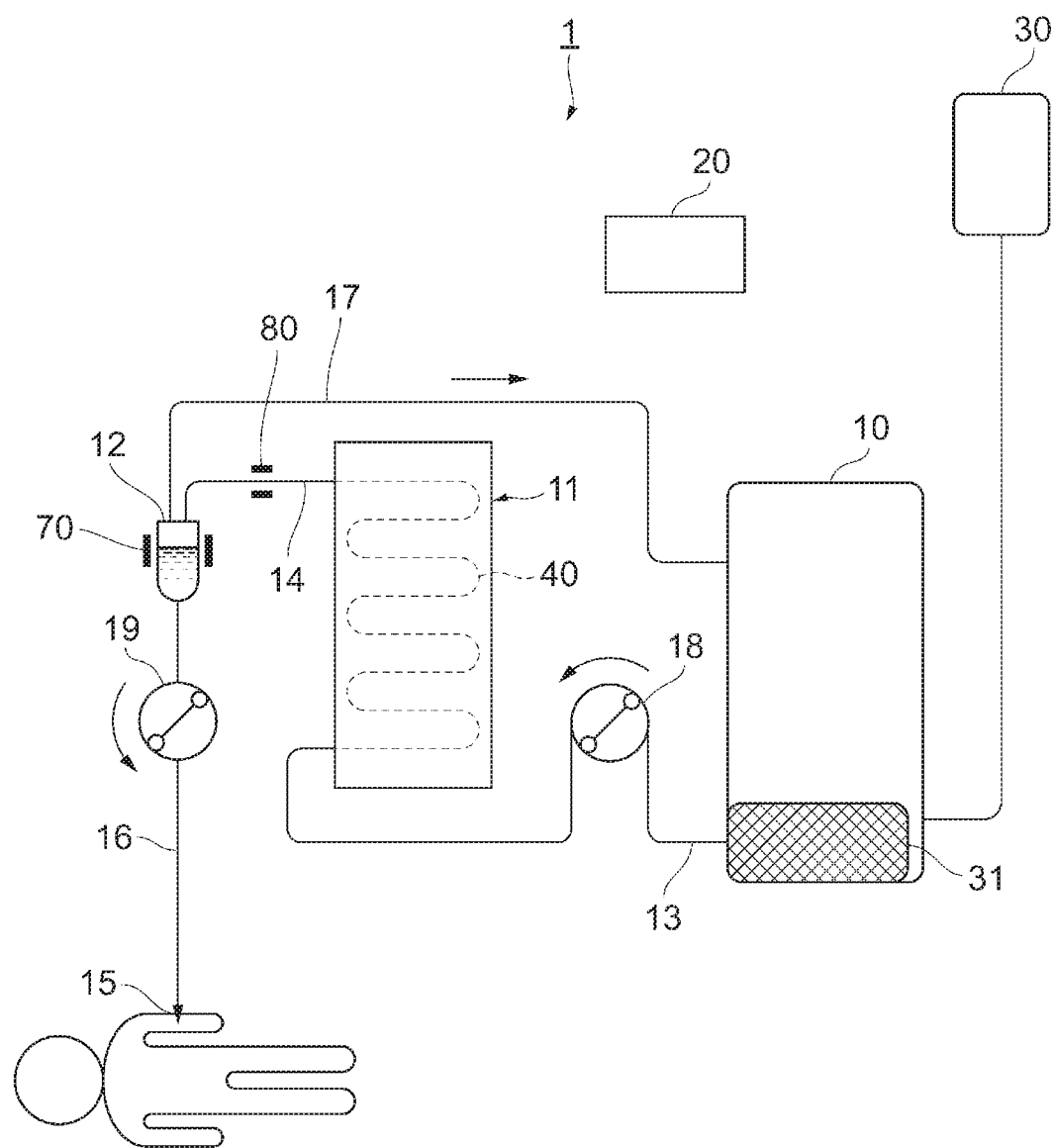
FIG. 1 is a schematic view showing the outline of the configuration of an infusion system.

Hereinafter, a preferred embodiment of the present invention will be described with reference to the drawings. Note that the same elements will be denoted by the same symbols, and duplicated descriptions will be omitted. In addition, positional relationships in a vertical direction, a horizontal direction, or the like are based on positional relationships shown in the drawings unless otherwise specifically noted. Moreover, the dimensional ratios of the drawings are not limited to ratios shown in the drawings. Further, the following embodiment is exemplified for the purpose of describing the present invention, and the present invention is not limited to the embodiment.

FIG. 1 shows an example of the configuration of an infusion system 1. As shown in FIG. 1, the infusion system 1 includes: a liquid container 10 that accommodates a blood derivative as a liquid for infusion; a heating device 11 that heats the blood derivative; an air bubble removal chamber 12 that removes air bubbles in the blood derivative; a first flow path 13 that connects the liquid container 10 and the heating device 11 to each other; a second flow path 14 that connects the heating device 11 and the air bubble removal chamber 12 to each other; a third flow path 16 that connects the air bubble removal chamber 12 and an infusion unit 15 that performs infusion for a patient to each other; a fourth flow path 17 that connects the air bubble removal chamber 12 and the liquid container 10 to each other; a first pump 18 provided in the first flow path 13; a second pump 19 provided in the third path 16; a control device 20; or the like.

The liquid container 10 is connected to, for example, a liquid bag 30 that serves as the supply source of the blood derivative. The liquid container 10 is provided with a filter 31 that removes an unnecessary component of the blood derivative flowing out to the first flow path 13. The liquid container 10 is made of, for example, a resin, and has a capacity of, for example, 0.5 L or more.

Figure 2:
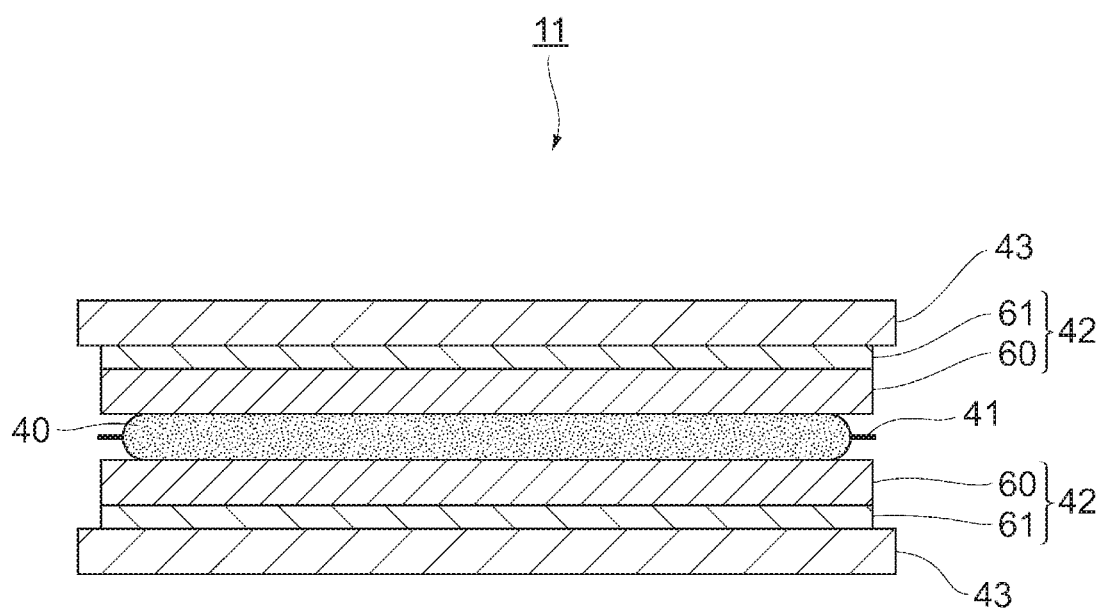
FIG. 2 is an explanatory view showing the outline of the configuration of a heating device.

As shown in FIG. 2, the heating device 11 includes: a heating unit 41 having a heating flow path 40 where the blood derivative flows; heat supply bodies 42 that contact the heating flow path 40 to supply heat; and heat insulation plates 43.

Figure 3:
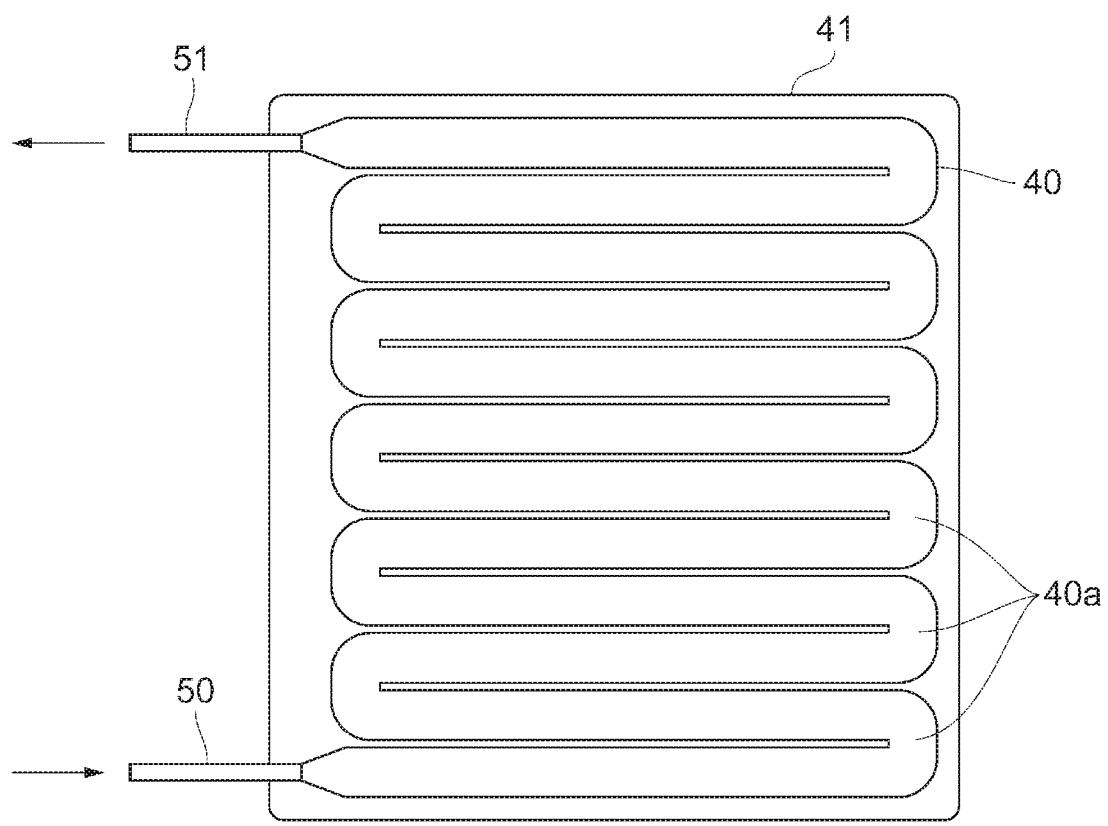
FIG. 3 is a schematic view showing the outline of the configuration of the heating unit of the heating device.

The heating unit 41 is made of a flexible resin, and formed into a square plate shape as shown in FIG. 3. The heating flow path 40 is configured to have, for example, a flexible tube shape, and formed to meander inside the heating unit 41. That is, the heating flow path 40 has a shape in which a plurality of reciprocating paths 40a are arranged from side to side and connected to each other. An inlet part 50 and an outlet part 51 of the heating flow path 40 are provided at, for example, ends in the same direction of the heating unit 41.

The heating flow path 40 has a flow path area of 200 $cm^2$ or more. Note that the "flow path area" represents the area of a portion contacting heat media (heat plates 60). In addition, the wall of the tube of the heating flow path 40 has a thickness of 0.4 mm or less, preferably a thickness of 0.3 mm or less, and further preferably a thickness of 0.2 mm or less.

As shown in FIG. 2, the heat supply bodies 42 have the respective heat plates 60, and heaters 61 that generate heat through heat supply. The heat plates 60 are formed into the same square plate shape as the heating unit 41. The heat plates 60 contact the heating flow path 40 of the heating unit 41. The heaters 61 are formed into a prescribed pattern along the heating flow path 40. The heat supply bodies 42 are arranged on, for example, both sides across the heating unit 41. The heat insulation plates 43 are arranged on the outside of the respective heat supply bodies 42.

As shown in FIG. 1, the air bubble removal chamber 12 has the second flow path 14 and the fourth flow path 17 connected thereto at its upper part, and has the third flow path 16 connected thereto at its lower part.

The air bubble removal chamber 12 is provided with a liquid level detector 70 that detects a liquid level. As the liquid level detector 70, a capacitance type sensor that detects a liquid level based on capacitance is, for example, used. Liquid level information detected by the liquid level detector 70 is output to the control device 20.

The first flow path 13, the second flow path 14, the third flow path 16, and the fourth flow path 17 are constituted by soft and flexible tubes. The second flow path 14 is provided with an air bubble detector 80 that detects air bubbles. As the air bubble detector 80, an ultrasonic type sensor that detects air bubbles based on ultrasonic waves is, for example, used. Air bubble information detected by the air bubble detector 80 is output to the control device 20.

As the first pump 18 and the second pump 19, tube pumps are, for example, used. The first pump 18 and the second pump 19 have a liquid feed capacity of, for example, 100 mL/min or more, preferably 250 mL/min or more, and further preferably 500 mL/min or more. The operations of the first pump 18 and the second pump 19 are controlled by the control device 20.

The control device 20 is, for example, a general-purpose computer, and runs a program recorded on a memory with a CPU to control the first pump 18, the second pump 19, the liquid level detector 70, the air bubble detector 80, or the like to enable the infusion operation of the infusion system 1.

The control device 20 controls each of a liquid feeding flow rate P1 of the first pump 18 and a liquid feeding flow rate P2 of the second pump 19. Generally, the liquid feeding flow rate P1 of the first pump 18 is controlled to be equal to or larger than the liquid feeding flow rate P2 of the second pump 19, the liquid feeding flow rate P2 of the second pump 19 is an infusion amount of the blood derivative to the infusion unit 15 patient) via the third flow path 16, and a difference (P1–P2) between the liquid feeding flow rate P1 of the first pump 18 and the liquid feeding flow rate P2 of the second pump 19 is a fluid flow rate from the air bubble removal chamber 12 to the liquid container 10 via the fourth flow path 17. In this case, the control device 20 may control the fluid flow rate from the air bubble removal chamber 12 to the liquid container 10 by, for example, making the liquid feeding flow rate P2 of the second pump 19 constant and controlling the liquid feeding flow rate P1 of the first pump 18. Note that a fluid in this case contains the blood derivative and gas caught by the air bubble removal chamber 12.

The control device 20 controls the liquid feeding flow rate of the first pump 18 based on, for example, the liquid level information of the air bubble removal chamber 12 detected by the liquid level detector 70. For example, when the liquid level of the air bubble removal chamber 12 is lower than a prescribed threshold, the control device 20 increases the liquid feeding flow rate of the first pump 18 to remove gas in the air bubble removal chamber 12. In addition, when the liquid level of the air bubble removal chamber 12 is lower than the threshold even if the liquid feeding flow rate of the first pump 18 is set at the upper limit of the pump, the control device 20 decreases the flow rate of the second pump 19 to remove gas in the air bubble removal chamber 12.

The control device 20 controls the liquid feeding flow rate of the first pump 18 based on, for example, air bubble information detected by the air bubble detector 80. For example, when plenty of air bubbles are detected by the air bubble detector 80, the control device 20 increases the liquid feeding flow rate of the first pump 18 to return a fluid from the air bubble removal chamber 12 to the liquid container 10. More specifically, the control device 20 calculates air bubble passage rate A per unit time in the second flow path 14 from air bubble information detected by the air bubble detector 80, and calculates an air bubble passage amount B (A×the liquid feeding flow rate of the first pump 18) of air bubbles passing per unit time in the second flow path 14 from the air bubble passage rate A. When the air bubble passage amount B is larger than a prescribed threshold, the control device 20 increases the flow rate of the first pump 18 according to an amount of the air bubble passage amount B and increases the flow rate of a fluid returned from the air bubble removal chamber 12 to the liquid container 10 to remove air bubbles. In addition, when the air bubble passage amount B is larger than the prescribed threshold even if the liquid feeding flow rate of the first pump 18 is set at the upper limit of the pump, the control device 20 decreases the flow rate of the second pump 19 to increase the flow rate of the fluid returned from the air bubble removal chamber 12 to the liquid container 10.

Next, the operation of the infusion system 1 thus configured will be described. First, the liquid bag 30 in which a low-temperature blood derivative is stored is connected to the liquid container 10, and the blood derivative of the liquid bag 30 is stored in the liquid container 10. Then, the first pump 18 and the second pump 19 operate, and the blood derivative of the liquid container 10 is fed to the heating device 11 via the first flow path 13. In the heating device 11, the blood derivative passes through the heating flow path 40. In this case, the blood derivative is heated to a prescribed temperature close to a body temperature by the heat plates 60 that use the heaters 61 as heat sources. The blood derivative heated by the heating device 11 passes through the second flow path 14 and flows into the air bubble removal chamber 12. Then, the blood derivative is caused to pass through the third flow path 16 by the second pump 19 and infused into a patient from the infusion unit 15. An infusion amount to the patient is controlled by the adjustment of the liquid feeding flow rate of the second pump 19.

Air bubbles occurring in the blood derivative in the heating device 11 are caught by the air bubble removal chamber 12. Some of the blood derivative and gas inside the air bubble removal chamber 12 are returned to the liquid container 10 via the fourth flow path 17. The flow rate of a fluid containing the gas passing through the fourth flow path 17 is controlled by the adjustment of the liquid feeding flow rate of the first pump 18. For example, the flow rate of the fluid flowing out from the air bubble removal chamber 12 to the fourth flow path 17 increases with an increase in the liquid feeding flow rate of the first pump 18, and the flow rate of the liquid flowing out from the air bubble removal chamber 12 to the fourth flow path 17 decreases with a decrease in the liquid feeding flow rate of the first pump 18. For example, when the liquid level of the air bubble removal chamber 12 detected by the liquid level detector 70 is lower than a prescribed threshold, the liquid feeding flow rate of the first pump 18 is increased to remove gas in the air bubble removal chamber 12. In addition, when air bubbles are detected by the air bubble detector 80, the liquid feeding flow rate of the first pump 18 is increased to remove gas accumulated in the air bubble removal chamber 12.

According to the present embodiment, the provision of the first pump 18 in the first flow path 13 and the second pump 19 in the third flow path 16 enables liquid feeding via the heating flow path 40 and liquid feeding from the air bubble removal chamber 12 to a patient to be shared by the different pumps. Therefore, the liquid feeding pressure of the first pump 18 can be decreased, and the internal pressure of the heating flow path 40 can be decreased. As a result, a structure that presses the heating flow path 40 in the heating device 11 can be simplified, and the weight of the heating device 11 can be suppressed.

In addition, when an infusion amount to a patient is decreased, the liquid feeding flow rate of the second pump 19 is only required to be changed but the liquid feeding flow rate of the first pump 18 is not required to be changed. Therefore, the flow rate of a blood derivative passing through the heating flow path 40 does not fluctuate, and the temperature of the blood derivative of the heating flow path 40 does not irregularly fluctuate under the influence of surrounding heat. As a result, the temperature control of the blood derivative can be properly performed in response to the fluctuation of an infusion amount. In particular, heating of the blood derivative to its upper limit temperature due to the penetration of high volumes of surrounding heat to the blood derivative in the heating flow path 40 is prevented.

The flow rate of a fluid returned from the air bubble removal chamber 12 to the liquid container 10 via the fourth flow path 17 can be adjusted by the change of the liquid feeding flow rate of the first pump 18. Therefore, when a large amount of air bubbles occur in the air bubble removal chamber 12, the liquid feeding flow rate of the first pump 18 is only required to be increased and the removal of the air bubbles can be performed without stopping infusion.

Since the air bubble detector 80 that detects air bubbles is provided in the second flow path 14, the liquid feeding flow rate of the first pump 18 is increased by the control device 20, for example, when a large amount of air bubbles are detected by the air bubble detector 80, whereby the gas of the air bubble removal chamber 12 can be removed to the liquid container 10 via the fourth flow path 17.

Since the liquid level detector 70 that detects a liquid level is provided in the air bubble removal chamber 12, the liquid feeding flow rate of the first pump 18 is increased by the control device 20 when, for example, the liquid level detected by the liquid level detector 70 is lower than a prescribed threshold, whereby the gas of the air bubble removal chamber 12 can be removed to the liquid container 10 via the fourth flow path 17.

With a high liquid feeding capacity of 100 mL/min or more, the first pump 18 and the second pump 19 can decrease the internal pressure of the heating flow path 40 particularly when used in a high pressure region and thus are preferable.

In addition, the heating flow path 40 is constituted by a flexible tube, and the flexible tube of the heating flow path 40 has a thickness of 0.4 mm or less. In this case, since the heating flow path 40 has high heating performance but has low pressure resisting performance. Therefore, an advantage that an increase in the internal pressure of the heating flow path 40 is suppressed by the first pump 18 and the second pump 19 in a shared manner as in the present invention becomes large.

Since the heating flow path 40 has a flow path area of 200 cm$^2$ or more, a load (a heating flow path area×an internal pressure inside the heating flow path) applied from the heating flow path 40 to the body of the heating device 11 is liable to increase. Therefore, the advantage that the increase in the internal pressure of the heating flow path 40 is suppressed by the first pump 18 and the second pump 19 in a shared manner as in the present invention becomes large.

The preferred embodiment of the present invention is described above with reference to the accompanying drawings, but the present invention is not limited to such an example. It is evident that those skilled in the art could conceive various modified examples or corrected examples within the scope of the spirit described in claims, and it is understood that such modified examples or corrected examples belong to the technical scope of the present invention as a matter of course.

For example, the infusion system 1 has the liquid level detector 70 and the air bubble detector 80 in the above embodiment, but the liquid level detector 70 and the air bubble detector 80 may not be necessarily provided. The configuration of the heating device 11 is not limited to the above example. The liquid for infusion fed in the infusion system 1 includes but not limited to a blood derivative. For example, the liquid for infusion may be fresh frozen plasma (FFP), albumin, an extracellular fluid, or the like.

INDUSTRIAL APPLICABILITY

The present invention is useful for providing an infusion system capable of decreasing the internal pressure of a heating flow path, properly performing the temperature control of a liquid for infusion in response to the fluctuation of an infusion amount, and performing the removal of air bubbles without stopping infusion.

REFERENCE SIGNS LIST

1 Infusion system
10 Liquid container
11 Heating device
12 Air bubble removal chamber
13 First flow path
14 Second flow path
15 Infusion unit
16 Third flow path
17 Fourth flow path
18 First pump
19 Second pump
20 Control device
40 Heating flow path
42 Heat supply body

What is claimed is:

1. An infusion system comprising:
a liquid container that accommodates a liquid for infusion;
a heating device that heats the liquid;
an air bubble removal chamber that removes air bubbles in the liquid;
a first flow path that connects the liquid container and the heating device to each other;
a second flow path that connects the heating device and the air bubble removal chamber to each other;
a third flow path that connects the air bubble removal chamber and an infusion unit, which performs the infusion, to each other, wherein all of the liquid passing through an outlet of the third flow path is supplied to the infusion unit;
a fourth flow path that connects the air bubble removal chamber and the liquid container to each other, the fourth flow path being devoid of any other structure;
a first pump provided in the first flow path;
a second pump provided in the third flow path, wherein the heating device has a heating flow path where the liquid flows and a heat supply body that contacts the heating flow path to supply heat to the heating flow path, and
a controller that controls the infusion system such that a liquid feeding flow rate of the first pump is equal to or larger than a liquid feeding flow rate of the second pump,
wherein a difference between the liquid feeding flow rate of the first pump and the liquid feeding flow rate of the second pump is a fluid flow rate from the air bubble removal chamber to the liquid container via the fourth flow path.

2. The infusion system according to claim 1, further comprising an air bubble detector that detects the air bubbles passing through the second flow path.

3. The infusion system according to claim 2, wherein the controller controls the first pump to increase the liquid feeding flow rate of the first pump when the air bubbles are detected by the air bubble detector.

4. The infusion system according to claim 3, wherein the heating flow path has a flow path area of 200 cm$^2$ or more.

5. The infusion system according to claim 2, wherein the heating flow path has a flow path area of 200 cm$^2$ or more.

6. The infusion system according to claim 1, further comprising a liquid level detector that detects a liquid level inside the air bubble removal chamber.

7. The infusion system according to claim 6, wherein the controller controls the first pump to increase the liquid feeding flow rate of the first pump when the liquid level detected by the liquid level detector is lower than a prescribed threshold.

8. The infusion system according to claim 7, wherein the heating flow path has a flow path area of 200 $cm^2$ or more.

9. The infusion system according to claim 4, wherein the heating flow path has a flow path area of 200 $cm^2$ or more.

10. The infusion system according to claim 1, wherein the first pump and the second pump have a liquid feeding capacity of 100 mL/min or more.

11. The infusion system according to claim 10, wherein the heating flow path has a flow path area of 200 $cm^2$ or more.

12. The infusion system according to claim 1, wherein the heating flow path is constituted by a flexible tube.

13. The infusion system according to claim 12, wherein the flexible tube has a thickness of 0.4 mm or less.

14. The infusion system according to claim 13, wherein the heating flow path has a flow path area of 200 $cm^2$ or more.

15. The infusion system according to claim 12, wherein the heating flow path has a flow path area of 200 $cm^2$ or more.

16. The infusion system according to claim 1, wherein the heating flow path has a flow path area of 200 $cm^2$ or more.

* * * * *

UNITED STATES PATENT AND TRADEMARK OFFICE
CERTIFICATE OF CORRECTION

PATENT NO. : 11,413,403 B2
APPLICATION NO. : 16/318913
DATED : August 16, 2022
INVENTOR(S) : N. Yoshioka et al.

It is certified that error appears in the above-identified patent and that said Letters Patent is hereby corrected as shown below:

In the Claims

At Column 9 (Claim 9, Line 1), please change "claim 4" to -- claim 6 --.

Signed and Sealed this
Thirteenth Day of June, 2023

Katherine Kelly Vidal
*Director of the United States Patent and Trademark Office*